Feb. 23, 1960 F. MEILLAND Plant Pat. 1,911
ROSE PLANT
Filed Jan. 8, 1959
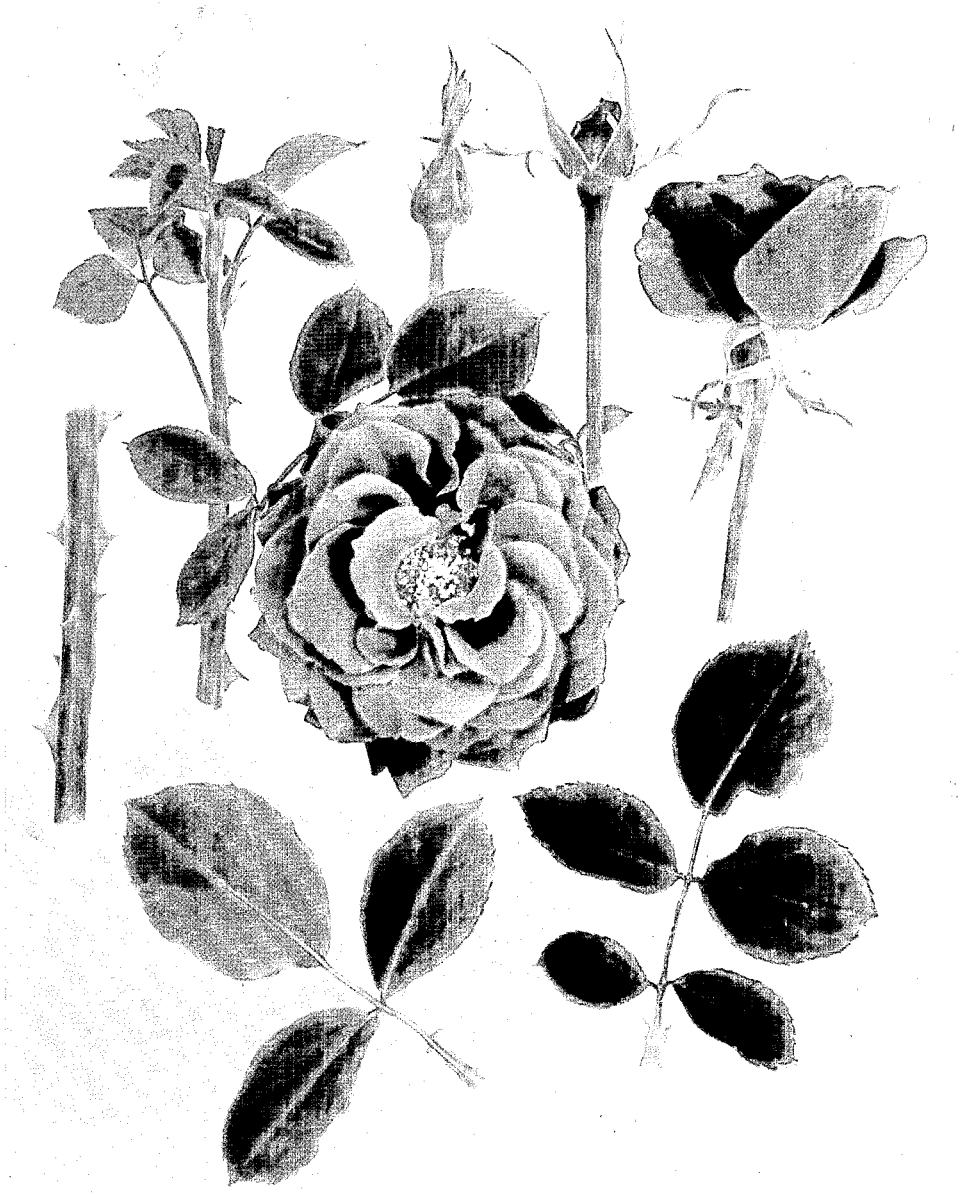
Inventor.
Francis Meilland, Deceased
By: Marie Louise Meilland, née Paolino
Legal Representative
By: Robb & Robb, Attorneys.

United States Patent Office

Plant Pat. 1,911
Patented Feb. 23, 1960

1,911

ROSE PLANT

Francis Meilland, deceased, late of Cap d'Antibes, France, by Marie Louise Meilland, nee Paolino, legal representative, Cap d'Antibes, France Application January 8, 1959, Serial No. 785,767

1 Claim. (Cl. 47—61)

The present invention relates to a new and distinct variety of rose plant of the hybrid tea class, which was originated by the deceased by crossing an unnamed and unpatented seedling of "Happiness"—known in France as "Rouge Meilland" (U.S. Plant Patent No. 911) × "Independence"—known in Germany as "Sondermeldung" (U.S. Plant Patent No. 1036) with an unnamed and unpatented seedling of "Happiness" × "Floradora" (unpatented).

The primary objective of this breeding was to produce a new red rose variety which combines the flower form of the parent variety "Happiness" with the orange and orange-scarlet flower color tones of "Independence" and "Floradora." While the parents of the new variety exhibited some of the desired objectives, each lacked certain qualities which would make them worthy of commercial interest, and the deceased therefore sought to fully achieve the desired objectives by a carefully planned breeding program. These objectives were ultimately fully achieved in the new variety, along with other desirable improvements, as evidenced by the following unique combination of characteristics which are outstanding in the new variety and which distinguish it from its parents as well as from all other varieties of which the deceased was aware:

(1) An excellent bloom form;

(2) A fine and tough petal texture which is unusual for a red rose; and (3) An intense, velvety cardinal red general color tonality of the blooms, overlaid with maroon.

Asexual reproduction of the new variety by budding, as performed in France and also at West Grove, Pennsylvania, U.S.A., shows that the foregoing characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for cut flowers and for garden decoration.

Class: Hybrid tea.

Breeding: Seedling.

*Seed parent.*—An unnamed seedling of "Happiness" × "Independence."

*Pollen parent.*—An unnamed seedling of "Happiness" × "Floradora."

Propagation: Holds its distinguishing characteristics through succeeding propagations by budding.

*Flower*

Locality where grown and observed: West Grove, Pennsylvania, U.S.A.

Flowers borne: Usually singly to stem, but sometimes several to stem; on stems of medium length and from weak to normal strength.

Quantity of bloom: Free, outdoors.

Continuity: Continuous.

Fragrance: Slight.

Bud:

*Peduncle.*—Long; medium caliper; erect; rough; medium number of red hairs. Color—reddish.

*Before calyx breaks.*—Size—medium. Form—from short to medium length; ovoid; with a conspicuous neck; with foliaceous appendages on the surface of the bud; with slender, medium-cut foliaceous parts extending beyond the tip of the bud equal to ¾ or more of its length.

*As calyx breaks.*—Color—slightly darker than Maroon, Plate 1030.

*As first petal opens.*—Size—medium. Form—short; ovoid. Color: outside—Ruby Red, Plate 827; inside—a velvety Cardinal Red, Plate 822, overlaid with Maroon, Plate 1030.

*Opening.*—Opens up well.

Bloom:

*Size (when fully open).*—Large; from 4¼ inches to 5 inches.

*Petalage.*—Very double; from 55 to 65 petals; arranged regularly.

*Form.*—Full at first, but becoming high-centered; petals at first being very loosely rolled outward, but later becoming loosely rolled outward at maturity.

Petals: Medium thickness; leathery; with inside velvety and outside satiny. Shape: outer petals—obovate; usually with 1 notch; intermediate petals—obovate; with 1 notch; inner petals—obovate; with 1 or more notches.

This description of a newly opened flower was made from a rose grown outdoors in the month of October at West Grove, Pennsylvania, U.S.A.:

*Color.*—Outer petal: outside surface—Ruby Red, Plate 827; inside surface—a velvety Cardinal Red, Plate 822, overlaid with Maroon, Plate 1030. Intermediate petal: outside surface—Chrysanthemum Crimson, Plate 824/2; inside surface—intermediate between Cherry, Plate 722 and Cardinal Red, Plate 822, with an iridescent appearance. Inner petal: outside surface—Chrysanthemum Crimson, Plate 824/2; inside surface—intermediate between Cherry, Plate 722 and Cardinal Red, Plate 822, with an iridescent appearance.

This description was made from a rose that was open for 3 days outdoors in the month of October, at West Grove, Pennsylvania, U.S.A.:

*Color.*—Outer petal: outside surface—Chrysanthemum Crimson, Plate 824/2; inside surface—intermediate between Rose Red, Plate 724 and Chrysanthemum Crimson, Plate 824, with an iridescent appearance. Inner petal: outside surface—Rose Red, Plate 724, sometimes streaked with Rhodamine Pink, Plate 527; inside surface—intermediate between Rose Red, Plate 724 and Chrysanthemum Crimson, Plate 824, with a velvety iridescent appearance.

*General color effect.*—Newly opened flower—a velvety Cardinal Red, Plate 822, overlaid with Maroon, Plate 1030. 3-days open—intermediate between Rose Red, Plate 724 and Chrysanthemum Crimson, Plate 824, with an iridescent appearance.

*Behavior.*—Drop off cleanly.

*Flower longevity.*—On bush in garden—4 days in June. Cut roses grown outdoors and kept at living-room temperatures—5 days in June.

*Reproductive organs*

Stamens: Medium number; arranged regularly about pistils.

Filaments: Most with anthers; medium length. Color—Rhodonite Red. Plate 0022/1, with base Aureolin, Plate 3/2.

Anthers: All open at once; medium size; seldom an anther fused with a petaloid. Color—Rhodonite Red, Plate 0022.

Pollen: Moderate abundance. Color—gold.

Pistils: Medium number.

Styles: Uneven; medium length; medium heavy; loosely bunched.

Stigma: Color—white.

Ovaries: All enclosed in receptacle.

Hips: None observed.

Sepals: Permanent; very long; spear-shaped; sometimes partly recurved.

Seeds: None observed.

*Plant*

Foliage:

*Leaves.*—Compound of 5 leaflets; from normal abundance to abundant; moderately large; leathery.

*Leaflets.*—Shape—almost round, with apex acuminate. Base—round. Margin—simply serrate.

*Color.*—Mature: upper surface—Parsley Green, Plate 00962; under surface—Willow Green, Plate 000862. Young: upper surface—Oxblood Red. Plate 00823; under surface—Oxblood Red, Plate 00823/3.

*Rachis (the supporting stem of the compound leaf).*—Medium caliper. Upper side—grooved; hairy. Under side—smooth.

*Stipules.*—Moderately long; medium width; with points of medium length turning out at an angle of more than 45°.

*Disease resistance.*—Comparable to that of the average variety grown under the same cultural conditions at West Grove, Pennsylvania, U.S.A.

Growth:

*Habit.*—Bushy; upright; much-branched.

*Growth.*—Vigorous.

*Canes.*—Medium caliper.

*Main stems.*—Bright. Color—Fern Green, Plate 0862. Prickles—several; color—Brick Red, Plate 016. Hairs—none.

*Branches.*—Bright. Color—Fern Green, Plate 0862. Prickles—several; color—Garnet Brown, Plate 00918/3. Hairs—none.

*New shoots.*—Dull. Color—Oxblood Red, Plate 00823. Prickles—several; color—Oxblood Red, Plate 00823. Hairs—None.

What is claimed is:

A new and distinct variety of rose plant of the hybrid tea class, substantially as herein shown and described, characterized particularly as to novelty by the unique combination of excellent flower form, an unusually fine and tough petal texture, and an intense, velvety Cardinal Red general color tonality of the blooms, overlaid with Maroon.

No references cited.